(12) United States Patent
Hu et al.

(10) Patent No.: US 11,514,621 B2
(45) Date of Patent: Nov. 29, 2022

(54) LOW-DOSE IMAGE RECONSTRUCTION METHOD AND SYSTEM BASED ON PRIOR ANATOMICAL STRUCTURE DIFFERENCE

(71) Applicant: SHENZHEN INSTITUTES OF ADVANCED TECHNOLOGY, Guangdong (CN)

(72) Inventors: Zhan Li Hu, Guangdong (CN); Dong Liang, Guangdong (CN); Hai Rong Zheng, Guangdong (CN); Xin Liu, Guangdong (CN); Yong Feng Yang, Guangdong (CN); Zhen Xing Huang, Guangdong (CN)

(73) Assignee: SHENZHEN INSTITUTES OF ADVANCED TECHNOLOGY, Guangdong (CN)

( * ) Notice: Subject to any disclaimer, the term of this patent is extended or adjusted under 35 U.S.C. 154(b) by 420 days.

(21) Appl. No.: 16/878,633

(22) Filed: May 20, 2020

(65) Prior Publication Data

US 2021/0192806 A1    Jun. 24, 2021

Related U.S. Application Data

(63) Continuation-in-part of application No. PCT/CN2019/126411, filed on Dec. 18, 2019.

(51) Int. Cl.
*G06T 11/00* (2006.01)
*A61N 5/10* (2006.01)

(52) U.S. Cl.
CPC .......... *G06T 11/003* (2013.01); *G06T 11/008* (2013.01); *A61N 5/1049* (2013.01); *A61N 2005/1062* (2013.01)

(58) Field of Classification Search
CPC .... G06T 11/003; G06T 11/008; G06T 11/006; A61N 5/1049; A61N 2005/1062
See application file for complete search history.

(56) References Cited

U.S. PATENT DOCUMENTS 11,126,914 B2 * 9/2021 Thibault ............. G01N 23/046

* cited by examiner

*Primary Examiner* — Courtney D Thomas
(74) *Attorney, Agent, or Firm* — JCIP Global Inc.

(57) ABSTRACT

The disclosure provides a low-dose image reconstruction method and system based on prior anatomical structure difference. The method includes: determining the weights of different parts in the low-dose image based on prior information of anatomical structure differences; constructing a generative network being taking the low-dose image as input extract features, and integrating the weights of the different parts in the feature extraction process, outputting a predicted image; constructing a determining network being taking the predicted image and standard-dose image as input, to distinguish the authenticity of the predicted image and standard-dose image as the first optimization goal, and identifying different parts of the predicted image as the second optimization goal, collaboratively training the generative network and the determining network to obtain the mapping relationship between the low-dose image and the standard-dose image; and reconstructing the low-dose image by using the obtained mapping relationship. The disclosure can obtain more accurate high-definition images.

10 Claims, 4 Drawing Sheets

LOW-DOSE IMAGE RECONSTRUCTION METHOD AND SYSTEM BASED ON PRIOR ANATOMICAL STRUCTURE DIFFERENCE

CROSS-REFERENCE TO RELATED APPLICATION

This application is a continuation in part of international PCT application serial no. PCT/CN2019/126411, filed on Dec. 18, 2019. The entirety of the above-mentioned patent application is hereby incorporated by reference herein and made a part of this specification.

BACKGROUND

Technical Field

The disclosure relates to the technical field of medical image processing, in particular to a low-dose image reconstruction method and system based on prior anatomical structure differences.

Description of Related Art

Computer tomography (CT) is an important imaging method for obtaining information on the internal structure of objects through non-destructive methods. CT has many advantages such as high resolution, high sensitivity and multiple levels, and is commonly used in various medical clinical examination fields. However, due to the need to use X-rays in the CT scanning process, as people have realized the potential hazards of radiation, the issue of CT radiation dose has received getting more and more attention. The principle of as low as reasonably achievable (ALARA) requires that the radiation dose to patients be reduced as much as possible under the premise of satisfying clinical diagnosis. Therefore, research and development of new low-dose CT imaging methods can both ensure the quality of CT imaging and reduce harmful radiation doses, and have important scientific significance and application prospects in the field of medical diagnosis.

The main problem with existing low-dose image reconstruction methods is that full sampling is usually required, resulting in a long CT scan time. Due to the large amount of data collected for full sampling, the image reconstruction speed is slow; due to the long scan time, it leads to artifacts caused by patient's movement. Since most algorithms are designed based on a small number of parts, the algorithms have poor robustness, and the patient is subjected to a high CT radiation dose. In addition, when the solution of related art solves the low-dose CT imaging problem, it is overlooked that there are significant differences in the anatomical structures in low-dose images. For example, there are obvious anatomical structures in the cranial and abdominal structures, which affect the clarity of the reconstructed image.

SUMMARY

Technical Problem

The purpose of the disclosure is to overcome the above-mentioned defects of the related art, provide a low-dose image reconstruction method and system based on anatomical structure differences, and complete image reconstruction based on sparse projection sampling. The anatomical structure differences are taken into consideration, and the anatomical structure differences serve as prior information to be introduced into the network design, thus ensuring the clarity of the reconstructed image.

According to a first aspect of the disclosure, a low-dose image reconstruction method based on prior anatomical structure differences is provided. The method includes the following steps: determining the weights of different parts in low-dose images based on prior information of anatomical structure differences; constructing a generative network being taking the low-dose images as input extract features, and integrate the weights of different parts in the feature extraction process to output predicted images; constructing a determining network being taking the predicted image and the standard-dose image as input to distinguish the authenticity of the predicted image and the standard-dose image as the first optimization goal, and to identify the different parts of the predicted image as the second optimization goal, collaboratively train the generative network and the determining network to obtain the mapping relationship between the low-dose image and the standard-dose image; and reconstructing the low-dose image by using the obtained mapping relationship.

In an embodiment, the step of determining the weights of different parts in low-dose images based on prior information of anatomical structure differences includes the following sub-steps: constructing a weight prediction module including multiple convolution layers and Sigmod startup functions; and performing one-hot encoding on different parts of the low-dose image and sequentially input them to the plurality of convolutional layers, and then generating weights for different parts by using the Sigmod startup function.

In an embodiment, the generative network includes multiple cascading attribute augmentation modules for multiplying the features extracted from the input low-dose image and the weights of the different parts to obtain weight features, and the extracted features and weight features are integrated, wherein each attribute augmentation module includes a down-sampling layer, a ReLU layer, an up-sampling layer, a feature unifying layer, and a feature integration layer in sequence.

In an embodiment, the determining network includes a plurality of convolutional layers and two fully connected layers.

In an embodiment, the step of obtaining a mapping relationship between the low-dose image and the standard-dose image including assigning a training data set $D=\{(x_1, y_1), (x_2, y_2), \ldots, (x_n, y_n)\}$, wherein $x=\{x_1, x_2, \ldots, x_n\}$ is the image block extracted from the low-dose image, $y=\{y_1, y_2, \ldots, y_n\}$ is the image block extracted from the standard-dose image, $a=\{a_1, a_2, \ldots, a_n\}$ corresponds to the weight of different parts, and n is the total number of training samples. During the collaborative training process, the parameter $L_{MSE}$ in the generative network is obtained by minimizing the objective function of the mean square error, expressed as:

$$L_{MSE} = \frac{1}{n}\sum_{i=1}^{n} \|G(y_i; a_i; \ominus) - x_i\|_2^2$$

Wherein $\ominus$ represents the parameters of the generative network, and G represents the mapping of the generative network.

In an embodiment, a loss function $L_{WGAN}$ of the first optimization goal is set as:

$$L_{WGAN}=-E_x[D_d(x)]+E_y[D_d(G(y;x;\theta))]+\beta E_{\hat{x}}[(\|\Lambda_x D(\hat{x})\|_2-1)^2] \quad (4)$$

Wherein E represents the expectation calculation, β represents the balance factor, and $D_d$ represents the process of determining authenticity.

In an embodiment, a loss function $L_{Attribute}$ of the second optimization goal is set as:

$$L_{Attribute}=E_x(D_a(x)-a)+E_y(D_a(G(y;a;\theta))-a)$$

Wherein E represents the expectation calculation, and $D_a$ represents the process of determining the attributes of the parts.

According to a second aspect of the disclosure, a low-dose image reconstruction system based on prior anatomical structure differences is provided. The system includes a weight prediction module, a network construction and training module, and an image reconstruction module. The weight prediction module is configured to determine the weight of different parts in the low-dose image based on the prior information of anatomical structure differences; the network construction and training module is configured to construct a generative network, use the low-dose images as input extract features, and integrate the weights of different parts in the feature extraction process to output predicted images; and configured to construct a determining network, take the predicted image and the standard-dose image as input, so as to distinguish the authenticity of the predicted image and the standard-dose image as the first optimization goal, and to identify the different parts of the predicted image as the second optimization goal, collaboratively train the generative network and the determining network to obtain the mapping relationship between the low-dose image and the standard-dose image; and the image reconstruction module configured to reconstruct low-dose images by using the obtained mapping relationship.

Compared with the related art, the advantages of the disclosure are that, image content information and part information are integrated by utilizing the difference in anatomical structures, thereby improving the generative capability of network with respect to the anatomical structures; based on the adversarial network, attribute constraints are added to improve the perception of the network and anatomy. The disclosure improves the network performance, so that the reconstructed image retains the image details well, and the structure is clearer.

BRIEF DESCRIPTION OF THE DRAWINGS

The following drawings only schematically illustrate and explain the disclosure, and are not intended to limit the scope of the disclosure, wherein.

DESCRIPTION OF THE EMBODIMENTS

In order to make the purpose, technical solution, design method and advantages of the disclosure more clear, the disclosure will be further described in detail below through specific embodiments in conjunction with the accompanying drawings. It should be understood that the specific embodiments described herein are only used to explain the disclosure and are not intended to limit the disclosure.

In all examples shown and discussed herein, any specific values should be interpreted as merely exemplary and not limiting. Therefore, other examples of the exemplary embodiment may have different values.

Techniques, methods and equipment known to those of ordinary skill in the related art may not be discussed in detail, but where appropriate, the techniques, methods and equipment should be considered as part of the specification.

In short, the low-dose image reconstruction method based on prior anatomical structure differences provided by the embodiments of the disclosure takes into consideration the differences between anatomical structures of the input image, and the prior information (attribute) of introduced anatomical parts are added to the network framework in the form of weight. The same anatomical parts have the same weight, and different anatomical parts have different weights. In this manner, the data of multiple parts can be integrated on unified model framework. In order to improve the visual effect of the image, the Wasserstein generative adversarial network (WGAN) is introduced, and considering that the low-dose image and the estimated normal-dose image are derived from the same anatomical part, an attribute loss is proposed to define the attribute numerical distance between the estimated image and the real image. With various loss constraints, the low-dose image reconstruction method of the disclosure can obtain a clearer image.

Figure 1:
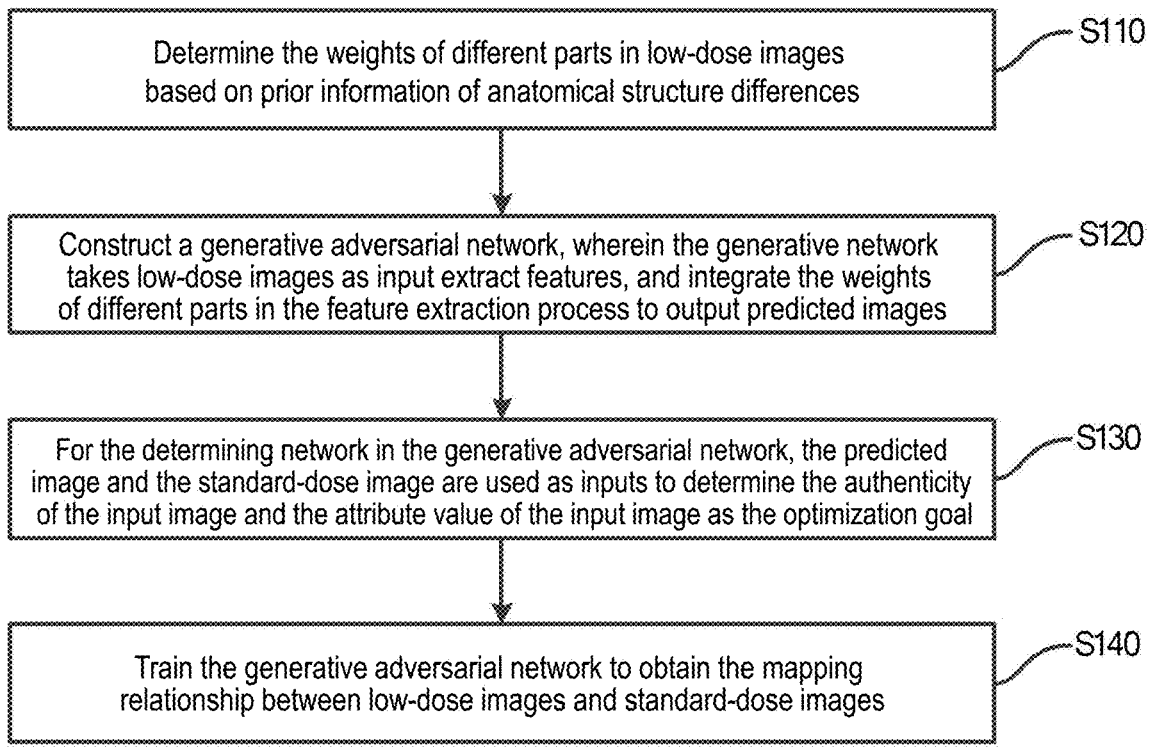
FIG. 1 is a flowchart of a low-dose image reconstruction method based on prior anatomical structure differences according to an embodiment of the disclosure.

Specifically, referring to FIG. 1, the low-dose image reconstruction method according to an embodiment of the disclosure includes the following steps:

In S110, the weights of different parts in low-dose images are determined based on prior information of anatomical structure differences.

Figure 2:
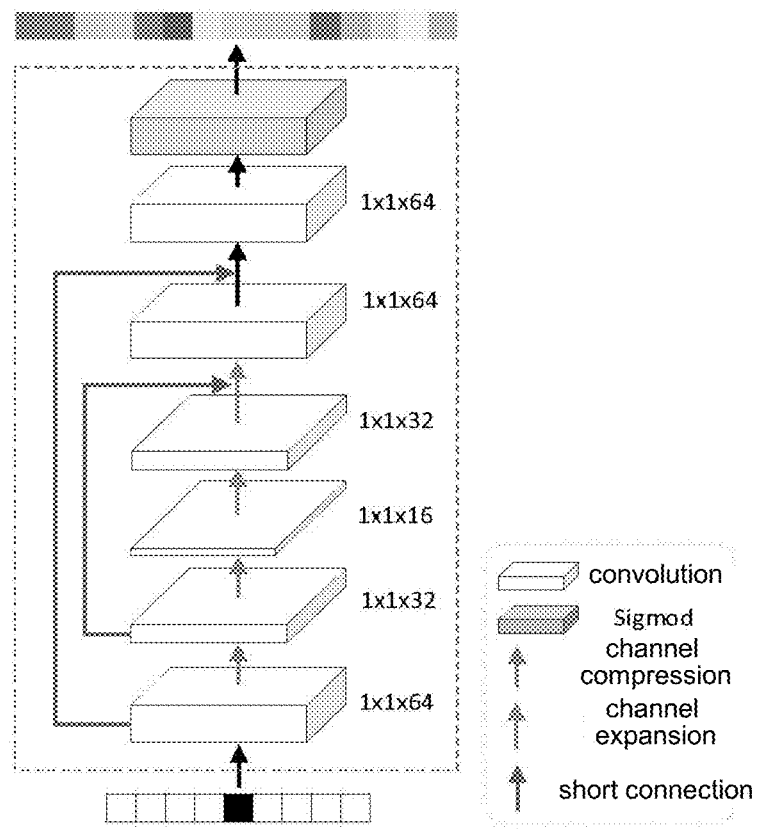
FIG. 2 is a schematic structural diagram of a weight prediction module according to an embodiment of the disclosure.

For example, the weights of different parts are determined according to the weight prediction module of FIG. 2. Each input low-dose image has a corresponding attribute (part), and firstly the attribute is subjected to one-hot encoding. 6 convolutional layers (convolution kernel 1×1) kernel are used, and finally the Sigmod startup function is utilized to generate a weight mask with 64 channels. Similar to the U-net structure, the compression and expansion of the channel are completed on the channel, and the short connection is utilized to connect the convolutional layers with the same number of channels to retain more context information, for example the first layer (1×1×64) and the fifth layer (1×1×64) from bottom to top in FIG. 2 use short connection, the second layer (1×1×32) and the fourth layer (1×1×32) use short connection. The weight prediction module can generate weights corresponding to each part according to the input attributes.

The structural parts referred to herein include, for example, the skull, orbit, sinuses, neck, lung cavity, abdomen, pelvis, knee, lumbar spine and so on.

It should be noted that, for the weight prediction module of FIG. 2, those skilled in the art can make appropriate modifications according to actual application scenarios, for example, by utilizing more or fewer convolutional layers, adopting other types of startup functions or setting more or fewer number of channels based on the number of parts in the low-dose image, such as a weight mask with 128 generated channels. In addition, in another embodiment, the weights of different parts can be simply set directly, as long as the different parts are differentiated and identified.

In step S120, a generative adversarial network is constructed, wherein the generative network takes low-dose images as input extract features and integrates the weights of different parts in the feature extraction process to output predicted images.

Figure 3:
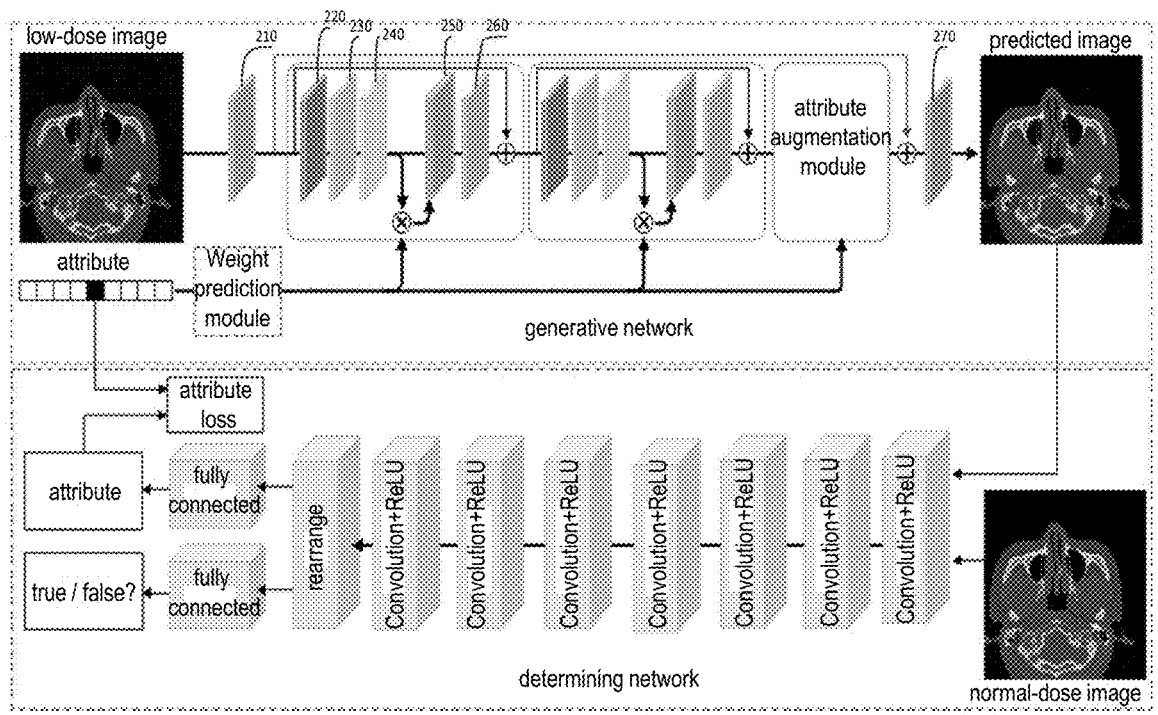
FIG. 3 is a schematic structural diagram of a generative adversarial network according to an embodiment of the disclosure.

As shown in FIG. 3, the overall generative adversarial network includes two parts: a generative network and a determining network, wherein the generative network includes a feature extraction layer 210, multiple cascading attribute augmentation modules (for example, 15 of which are provided) and a reconstruction layer 270. Each attribute augmentation module includes a down-sampling layer 220, a ReLU layer 230, an up-sampling layer 240, a feature unifying layer 250, and a feature integration layer 260. The attribute augmentation module completes feature extraction through the down-sampling layer 220, the ReLu layer 230, and the up-sampling layer 240, and then obtains part weights according to step S110, and the extracted features and weights are multiplied to obtain weight features. To prevent the loss of the original extracted features, the original feature and the weighted feature are combined by using a unifying layer, and feature integration is completed through the final feature integration layer 260 (such as a convolutional layer). The symbol ⊕ in FIG. 3 indicates dot addition, and ⊗ indicates dot multiplication.

In an embodiment, the parameter setting of the attribute augmentation module is shown in Table 1 below.

TABLE 1

Image augmentation module

| Unit | Operation | Parameter |
| --- | --- | --- |
| down-sampling layer | convolution | 3 × 3 × 64 |
| up-sampling layer | deconvolution | 3 × 3 × 64 |
| feature integration layer | convolution | 1 × 1 × 64 |

The input of the generative network constructed by the disclosure is a low-dose image, the input of the weight prediction module is the attribute corresponding to the low-dose image, and the output of the weight prediction module is the predicted weight of each part, wherein the weight of each part is multiplied with the original extracted features at the generative network, and finally the generative network outputs a predicted image.

In the embodiment of the disclosure, by setting the attribute augmentation module and the weight prediction module, the prior information of anatomical structure difference can be applied to the reconstruction of the low-dose image, thereby maintaining the characteristics of each part and increasing the difference of each part to make the predicted image to be more like the real image. The disclosure provides no limitation to the number of cascading attribute augmentation modules.

In step S130, for the determining network in the constructed generative adversarial network, the predicted image and the standard-dose image are used as inputs to determine the authenticity of the input image and the attribute value of the input image as the optimization goal.

Since the input low-dose image and the final estimated image have the same attributes, therefore, in addition to identifying the authenticity of the input image, the determining network also needs to identify the attribute value (i.e., part) of the input image. The input image of the framework of the entire generative adversarial network is an image block, and the size of the image block is, for example, 64×64. The training set and test set include images of multiple parts, such as the head, orbit, sinuses, neck, lung cavity, abdomen, pelvic cavity (male), pelvic cavity (female), knee, and lumbar spine.

In an embodiment, the determining network includes 7 convolutional layers and 2 fully connected layers. For specific parameter settings, see Table 2 below.

TABLE 2

Identify network parameters

| Unit | Convolution stride | Convolution kernel |
| --- | --- | --- |
| Convolutional layer 1 | 2 | 64 |
| Convolutional layer 2 | 1 | 128 |
| Convolutional layer 3 | 2 | 128 |
| Convolutional layer 4 | 1 | 256 |
| Convolutional layer 5 | 2 | 256 |
| Convolutional layer 6 | 1 | 512 |
| Convolutional layer 7 | 2 | 512 |
| Fully connected layer 1 | — | 1 |
| Fully connected layer 2 | — | 10 |

The input of the determining network is the predicted image and the normal-dose image obtained by the generative network. The output of the determining network includes two aspects, namely, determining the authenticity of the input image and identifying the attribute value of the input image. That is, the goal of the determining network is to try to distinguish the predicted image generated by the generative network from the real image, and accurately identify the attributes of the input image.

In step S140, the generative adversarial network is trained to obtain the mapping relationship between low-dose images and standard-dose images.

For example, assigning a training data set $D=\{(x_1, y_1), (x_2, \ldots, (x_n, y_n)\}$, wherein $x=\{x_1, x_2, \ldots, x_n\}$ is the image block extracted from the low-dose CT image, $y=\{y_1, y_2, \ldots, y_n\}$ is the image block extracted from the standard-dose CT image (i.e., normal-dose image), $a=\{a_1, a_2, \ldots, a_n\}$ is a corresponding attribute, and n is the number of training samples.

A supervision model is pre-trained, the parameter $L_{MSE}$ in the mapping G (generative network) can be obtained by minimizing the objective function of the mean square error, expressed as:

$$L_{MSE} = \frac{1}{n}\sum_{i=1}^{n} \|G(y_i; a_i; \Theta) - x_i\|_2^2 \qquad (1)$$

Wherein Θ represent network parameters (such as weight, offset, etc.).

In order to improve the visual effect, the adversarial loss function $L_{WGAN}$ is introduced to optimize the model to improve the accuracy of identifying the authenticity of the input image. The adversarial loss function $L_{WGAN}$ is expressed as:

$$L_{WGAN} = -E_x[D_d(x)] + E_y[D_d(G(y;x;\theta))] + \beta E_{\hat{x}}[(\|\Lambda_{\hat{x}} D(\hat{x})\|_2 - 1)^2] \qquad (2)$$

Wherein E stands for expectation calculation, β represents the balance factor to balance the adversarial loss and gradient penalty, and is set to 10 for example, and $D_d$ represents the process of determining the authenticity of the input image.

Further, for the process of identifying the attributes of the input image, because the input low-dose image and the estimated image have the same attributes, an attribute loss $L_{Attribute}$ is introduced to define the attribute distance between the estimated image and the original image. The attribute loss $L_{Attribute}$ is expressed as:

$$L_{Attribute}=E_x(D_a(x)-a)+E_y(D_a(G(y;a;\theta))-a) \quad (3)$$

Wherein E represents the expectation calculation, and $D_a$ represents the process of determining attributes.

It should be noted that in the process of collaboratively training the generative network and the determining network, the optimizer of existing technology can be adopted for optimization, for example, corresponding to the supervised learning (generative network), the Adam optimizer is utilized for optimization, and for the generative adversarial model, the SGD (stochastic gradient descent method) optimizer is utilized for optimization. During training, the image blocks are extracted from the dataset of standard-dose CT images and low-dose CT images for matching to be used with the corresponding attribute values as the overall network input. In addition, other forms of loss functions can also be used for training.

After training, the generative adversarial network obtains the mapping relationship G of the low-dose image to the standard-dose image, and the mapping relationship can be utilized to reconstruct the new low-dose image, thereby obtaining a clear image that is more like the real image.

Correspondingly, the disclosure provides a low-dose image reconstruction system based on prior anatomical structure differences, which is configured to implement one or more aspects of the above method. For example, the system includes a weight prediction module, which is configured to determine the weight of different parts in the low-dose image based on prior information of anatomical structure differences; a network construction and training module, which is configured to construct a generative network to use the low-dose image as the input extract features, and integrate the weights of different parts in the feature extraction process to output predicted images; and configured to construct a determining network using the predicted image and the standard-dose image as input to determine the authenticity of the predicted image and the standard-dose image as the first optimization goal, and identify different parts of the predicted image as the second optimization goal, collaboratively train the generative network and the determining network to obtain a mapping relationship between low-dose images and standard-dose images; an image reconstruction module, which is configured to reconstruct the low-dose image by using the obtained mapping relationship. Each module in the system provided by the disclosure can be implemented by a processor or a logic circuit.

It should be noted that in addition to CT image reconstruction, the disclosure can also be applied to PET (positron emission tomography), SPECT (single photon emission computed tomography) image reconstruction or other image reconstruction sampled based on sparse projection after proper modification.

Figure 4:
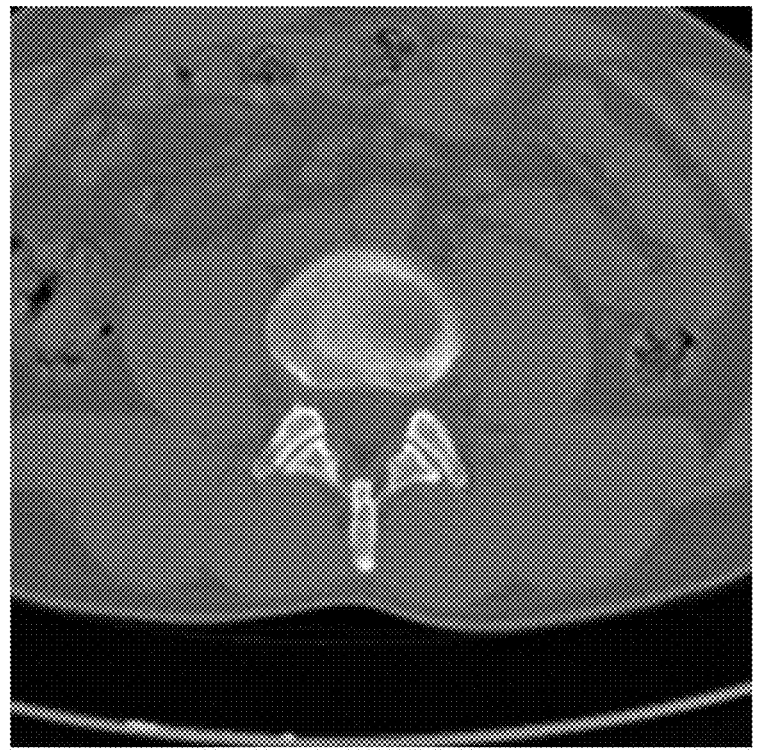
FIG. 4 is a schematic diagram of a reference standard image according to an embodiment of the disclosure.
Figure 5:
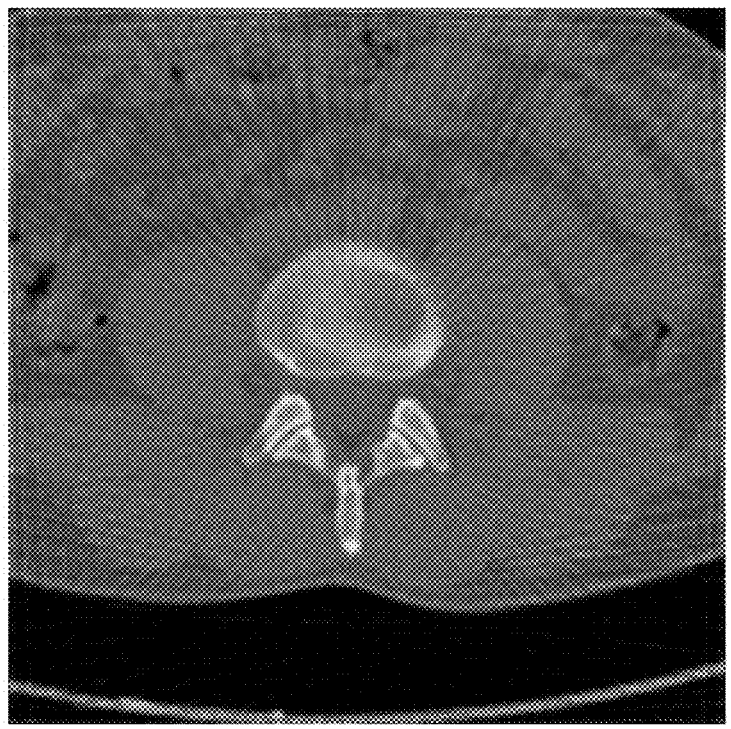
FIG. 5 is a schematic diagram of a sparsely sampled low-dose image according to an embodiment of the disclosure.
Figure 6:
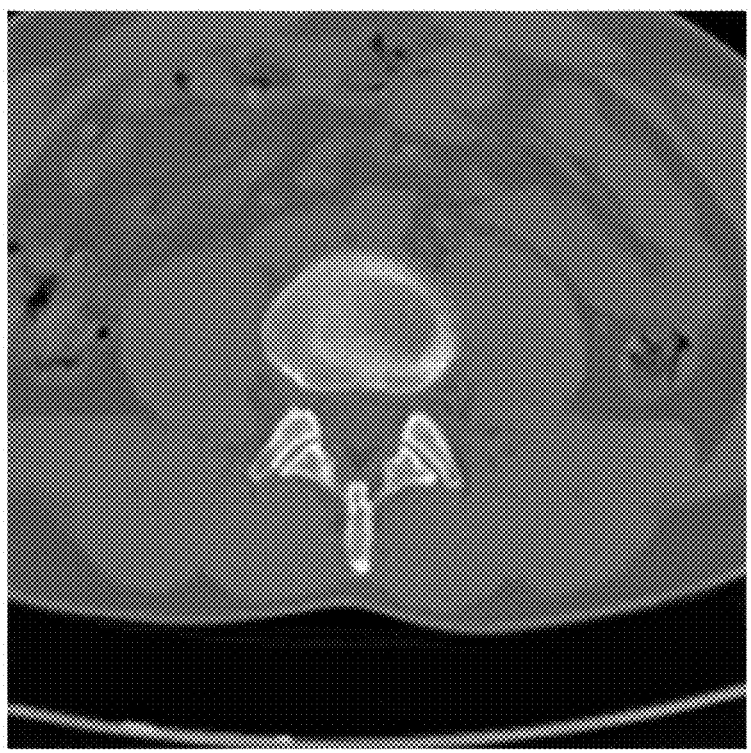
FIG. 6 is a schematic diagram of a reconstructed image according to an embodiment of the disclosure.

It has been verified that, by using the disclosure for image reconstruction, it is possible to obtain a clearer image with more details. Please refer to FIG. 4 to FIG. 6, FIG. 4 is a reference standard image, FIG. 5 is a sparsely sampled low-dose image, and FIG. 6 is a reconstructed image or a restored image.

In summary, the disclosure realizes the conversion of attribute values into weight masks through a weight prediction module, and completes the integration of original image features and attribute features by setting an attribute augmentation module in the generative network; defines attribute loss based on the same attribute value shared by the original low-dose images and the estimated images, so as to strengthen the constraint on the generative adversarial network and thus obtaining a more accurate high-definition image.

It should be noted that although the steps above are described in a specific order, it does not mean that the steps must be executed in the specific order described above. In fact, some of these steps can be executed concurrently or even changed in order as long as they can perform the required functions.

The disclosure may be a system, method and/or computer program product. The computer program product may include a computer non-transitory readable storage medium that is loaded with computer-readable program instructions for making the processor to implement various aspects of the disclosure.

The computer-readable storage medium may be a tangible device that holds and stores instructions used by the instruction execution device. The computer-readable storage medium may include, for example but not limited to, an electrical storage device, a magnetic storage device, an optical storage device, an electromagnetic storage device, a semiconductor storage device, or any suitable combination of the foregoing. More specific examples of computer-readable storage media (non-exhaustive list) include: portable computer disks, hard disks, random access memory (RAM), read-only memory (ROM), erasable and programmable program read-only memory (EPROM or flash memory), static random access memory (SRAM), portable compact disk read-only memory (CD-ROM), digital versatile disk (DVD), memory stick, Floppy disks, mechanical coding devices, such as punched cards or raised structures in grooves on which instructions are stored, and any suitable combination of the above.

The embodiments of the disclosure have been described above. The above description is exemplary, not exhaustive, and is not limited to the disclosed embodiments. Many modifications and changes will be apparent to those of ordinary skill in the art under the circumstances that the modifications and changes are not deviated from the scope and spirit of the embodiments of the disclosure. The selection of terms used herein is intended to best explain the principles, practical applications or technical improvements in the market of the embodiments, or to enable other ordinary skilled in the art to understand the embodiments disclosed herein.

What is claimed is:

1. A low-dose image reconstruction method based on prior anatomical structure differences, comprising:
   determining weights of different parts in a low-dose image based on prior information of anatomical structure differences;
   constructing a generative network being taking the low-dose image as an input extract feature, and integrating the weights of the different parts in a feature extraction process to output a predicted image;
   constructing a determining network being taking the predicted image and a standard-dose image as input to distinguish an authenticity of the predicted image and the standard-dose image as a first optimization goal, and identifying different parts of the predicted image as a second optimization goal, collaboratively training the generative network and the determining network to obtain a mapping relationship between the low-dose image and the standard-dose image; and reconstructing the low-dose image by using the obtained mapping relationship.

2. The low-dose image reconstruction method based on prior anatomical structure differences according to claim 1, wherein the step of determining the weights of the different parts in the low-dose image based on prior information of the anatomical structure difference comprising:

constructing a weight prediction module comprising a plurality of convolution layers and a Sigmod startup function; and performing one-hot encoding on different parts of the low-dose image and sequentially inputting them to the plurality of convolutional layers, and then generating weights for different parts by using the Sigmod startup function.

3. The low-dose image reconstruction method based on prior anatomical structure differences according to claim 1, wherein the generative network comprises multiple cascading attribute augmentation modules for multiplying features extracted from the input low-dose image and the weights of the different parts to obtain a weight feature, and the extracted feature and the weight feature are integrated, wherein each attribute augmentation module comprises a down-sampling layer, a ReLU layer, an up-sampling layer, a feature unifying layer, and a feature integration layer in sequence.

4. The low-dose image reconstruction method based on prior anatomical structure differences according to claim 1, wherein the determining network comprises a plurality of convolutional layers and two fully connected layers.

5. The low-dose image reconstruction method based on prior anatomical structure differences according to claim 1, wherein the step of obtaining a mapping relationship between the low-dose image and the standard-dose image comprising:

assigning a training data set $D=\{(x_1, y_1), (x_2, y_2), \ldots, (x_n, y_n)\}$, wherein $x=\{x_1, x_2, \ldots, x_n\}$ is an image block extracted from the low-dose image, $y=\{y_1, y_2, \ldots, y_n\}$ is an image block extracted from the standard-dose image, $a=\{a_1, a_2, \ldots, a_n\}$ corresponds to the weight of different parts, and n is the total number of training samples; and obtaining a parameter $L_{MSE}$ in the generative network by minimizing an objective function of mean square error during a collaborative training process, and the parameter $L_{MSE}$ expressed as:

$$L_{MSE} = \frac{1}{n}\sum_{i=1}^{n} \|G(y_i; a_i; \Theta) - x_i\|_2^2$$

wherein $\Theta$ represents the parameters of the generative network, and G represents the mapping of the generative network.

6. The low-dose image reconstruction method based on prior anatomical structure differences according to claim 5, wherein a loss function $L_{WGAN}$ of the first optimization goal is set as:

$$L_{WGAN}=-E_x[D_d(x)]+E_y[D_d(G(y;x;\theta))]+\beta E_{\hat{x}}[(\|\Lambda_{\hat{x}}D(\hat{x})\|_2-1)^2]$$

wherein E represents an expectation calculation, $\beta$ represents a balance factor, and $D_d$ represents a process of determining authenticity.

7. The low-dose image reconstruction method based on prior anatomical structure differences according to claim 5, wherein a loss function $L_{Attribute}$ of the second optimization goal is set as:

$$L_{Attribute}=E_x(D_a(x)-a)+E_y(D_a(G(y;a;\theta))-a)$$

wherein E represents an expectation calculation, and $D_a$ represents a process of determining attributes of parts.

8. A computer-readable storage medium storing a computer program, wherein the steps of the method claimed in claim 1 are realized when the program is executed by a processor.

9. A computer device, comprising a memory and a processor, a computer program capable of running on the processor is stored on the memory, wherein the steps of the method claimed in claim 1 are realized when the processor executes the program.

10. A low-dose image reconstruction system based on prior anatomical structure differences, comprising:

a weight prediction module configured to determine the weight of different parts in a low-dose image based on prior information of anatomical structure differences;

a network construction and training module configured to construct a generative network, use the low-dose images as input extract features, and integrate the weights of the different parts in a feature extraction process to output a predicted image; and configured to construct a determining network, take the predicted image and a standard-dose image as input, so as to distinguish the authenticity of the predicted image and the standard-dose image as a first optimization goal, and to identify different parts of the predicted image as a second optimization goal, collaboratively train the generative network and the determining network to obtain a mapping relationship between the low-dose image and the standard-dose image; and an image reconstruction module configured to reconstruct the low-dose image by using the obtained mapping relationship.

* * * * *